United States Patent [19]

Batcho

[11] 4,176,230
[45] Nov. 27, 1979

[54] 5-(6-ALKYLINDOL-3-YLMETHYLENE)-1,3-DIMETHYL-2-(METHYLIMINO)-4-IMIDAZOLIDINONES

[75] Inventor: Andrew D. Batcho, North Caldwell, N.J.

[73] Assignee: Hoffmann-La Roche Inc., Nutley, N.J.

[21] Appl. No.: 821,854

[22] Filed: Aug. 4, 1977

[51] Int. Cl.$^2$ .............................................. C07D 403/06
[52] U.S. Cl. .................................... 542/444; 542/451; 548/315; 548/316; 424/273 R
[58] Field of Search ................. 542/444, 451; 548/315, 548/316

[56] References Cited

U.S. PATENT DOCUMENTS 3,933,798   1/1976   Curtis et al. .......................... 542/444

OTHER PUBLICATIONS

Kazlauskas et al. "Aplysinopsin, A New Tryptophan Derivative from a Sponge," in Tetrahedron Letrs, No. 1, pp. 61-64, 1977.

Primary Examiner—Arthur P. Demers
Attorney, Agent, or Firm—Jon S. Saxe; George M. Gould; William G. Isgro

[57] ABSTRACT 5-(6-alkylindol-3-ylmethylene)-1,3-dimethyl-2-(methylimino)-4-imidazolidinones, prepared, inter alia, from the corresponding substituted indole-3-carboxaldehyde and dimethylcreatinine, are described. The imidazolidinones are useful as antidepressants.

3 Claims, No Drawings

5-(6-ALKYLINDOL-3-YLMETHYLENE)-1,3-DIMETHYL-2-(METHYLIMINO)-4-IMIDAZOLIDINONES

BRIEF SUMMARY OF THE INVENTION

The invention relates to a compound of the formula

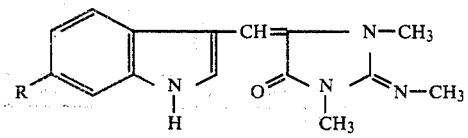

wherein R is lower alkyl, its geometric isomers and pharmaceutically acceptable acid addition salts thereof.

DETAILED DESCRIPTION OF THE INVENTION

The invention comprises a compound of the formula

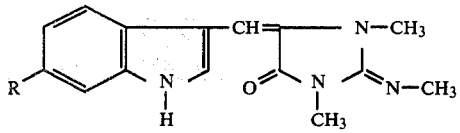

wherein R is lower alkyl of 1 to 7 carbon atoms, its geometric isomers and pharmaceutically acceptable acid addition salts thereof.

Examplary of the compounds of the invention are:
5-(6-methylindol-3-ylmethylene)-1,3-dimethyl-2-(methylimino)-4-imidazolidinone;
(3E)-5-(6-methylindol-3-ylmethylene)-1,3-dimethyl-2-(methylimino)-4-imidazolidinone;
(3Z)-5-(6-methylindol-3-ylmethylene)-1,3-dimethyl-2-(methylimino)-4-imidazolidinone;
5-(6-ethylindol-3-ylmethylene)-1,3-dimethyl-2-(methylimino)-4-imidazolidinone;
(3E)-5-(6-ethylindol-3-ylmethylene)-1,3-dimethyl-2-(methylimino)-4-imidazolidinone;
(3Z)-5-(6-ethylindol-3-ylmethylene)-1,3-dimethyl-2-(methylimino)-4-imidazolidinone;
5-(6-propylindol-3-ylmethylene)-1,3-dimethyl-2-(methylimino)-4-imidazolidinone;
(3E)-5-(6-propylindol-3-ylmethylene)-1,3-dimethyl-2-(methylimino)-4-imidazolidinone;
(3Z)-5-(6-propylindol-3-ylmethylene)-1,3-dimethyl-2-(methylimino)-4-imidazolidinone;
5-(6-isopropylindol-3-ylmethylene)-1,3-dimethyl-2-(methylimino)-4-imidazolidinone;
(3E)-5-(6-isopropylindol-3-ylmethylene)-1,3-dimethyl-2-(methylimino)-4-imidazolidinone;
(3Z)-5-(6-isopropylindol-3-ylmethylene)-1,3-dimethyl-2-(methylimino)-4-imidazolidinone;
5-(6-butylindol-3-ylmethylene)-1,3-dimethyl-2-(methylimino)-4-imidazolidinone;
(3E)-5-(6-butylindol-3-ylmethylene)-1,3-dimethyl-2-(methylimino)-4-imidazolidinone;
(3Z)-5-(6-butylindol-3-ylmethylene)-1,3-dimethyl-2-(methylimino)-4-imidazolidinone; and the like.

A preferred compound of the invention is (3E)-5-(6-methylindol-3-ylmethylene)-1,3-dimethyl-2-(methylimino)-4-imidazolidinone.

As already indicated, the compounds characterized by formula I can exist as geometric isomers and mixtures thereof. Individually, the geometric isomers can be characterized as the respective E isomer and the respective Z isomer. Generally, the isomers of a compound of formula I will exist in equilibrium in solution. Since the rate of equilibration is slow, such isomers can be recrystallized and can exist in the crystalline form as the E or the Z isomer. Separation of the isomers can be effected utilizing generally known procedures, such as, recrystallization from methanol/methylene chloride, acetonitrile or the like.

The compound of formula I of the invention can be prepared by reacting an indol carboxaldehyde of the formula

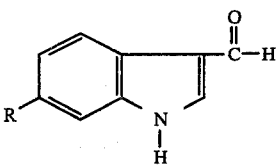

wherein R is lower alkyl, with dimethylcreatinine, i.e., 1,3-dimethyl-2-(methylimino)-4-imidazolidinone. Conveniently, a condensation catalyst, for example, a secondary or tertiary amine, such as, piperidine, or the like, or an aliphatic carboxylic acid and the alkali metal salt of said acid, such as acetic acid containing anhydrous sodium acetate or the like, can be utilized to carry out the reaction. The reaction temperature is not critical; preferably, the reaction is carried out at or near the reflux temperature of the reaction mixture. The reaction product, that is, a compound of formula I, can be recovered utilizing conventional procedures such as recrystallization or the like.

The compounds of formula I form acid addition salts and such salts are also within the scope of this invention. Thus, the compounds of formula I form pharmaceutically acceptable addition salts with, for example, both pharmaceutically acceptable organic and inorganic acids, such as, acetic acid, succinic acid, formic acid, methanesulfonic acid, p-toluenesulfonic acid, hydrochloric acid, phosphoric acid, sulfuric acid and the like.

The compounds of formula I of the invention have useful central nervous system activity. More particular, the compounds of formula I have antidepressant activity and are therefore useful as antidepressants. Such antidepressant activity can be demonstrated in warm-blooded animals. For example, mice are administered intraperitoneally 100 mg./kg. of tetrabenazine one hour after oral doses of the test compound. One hour later ptosis is scored. When (3E)-5-(6-methylindol-3-ylmethylene)-1,3-dimethyl-2-(methylimino)-4-imidazolidinone is utilized as the test compound, it demonstrates an $ED_{50}$ of 8.8 mg./kg.

For such use, the presently disclosed compounds, i.e., the compounds of formula I and their pharmaceutically acceptable acid addition salts are formulated, using conventional inert pharmaceutical adjuvant materials, into dosage forms which are suitable for oral or parenteral administration. Such dosage forms include tablets, suspensions, solutions, etc. Furthermore, the compounds of this invention can be embodied into, and administered in the form of, suitable hard or soft capsules. The identity of the inert adjuvant materials which are used in formulating the present compounds into oral and parenteral dosage forms will be immediately apparent to persons skilled in the art. These adjuvant materials, either inorganic or organic in nature, include, for example, water, gelatin, lactose, starch, magnesium stearate, talc, vegetable oils, gums, polyalkylene glycols, or the like. Moreover, preservatives, stabilizers, wetting agents, emulsifying agents, salts for altering osmotic pressure, buffers, or the like can be incorporated, if desired, into such formulations.

The compounds of formula I have antidepressant properties qualitatively similar to those of compounds, such as, imipramine, harmaline and pargyline, which are known for their therapeutic uses.

The following examples further illustrate the invention. All temperatures are in degrees centigrade, unless otherwise mentioned.

EXAMPLE 1

Preparation of (3E)-5-(6-Methylindol-3-ylmethylene)-1,3-dimethyl-2-(methylimino)-4-imidazolidinone A mixture of 4.77 g. of 6-methylindole-3-carboxaldehyde, 4.24 g. of dimethylcreatinine, and 50 ml. of piperidine was heated at reflux for 24 hours. The cooled suspension was poured into 250 ml. of water, and the yellow precipitate was collected by filtration, washed with water and dried in vacuo and afforded 7.0 g. of crude 5-(6-methylindol-3-ylmethylene)-1,3-dimethyl-2-(methylimino)-4-imidazolidinone. Recrystallization from acetonitrile gave 4.50 g. of (3E)-5-(6-methylindol-3-ylmethylene)-1,3-dimethyl-2-(methylimino)-4-imidazolidinone, melting point 227°–228°.

Calcd. for $C_{16}H_{18}N_4O$: C, 68.07; H, 6.43; N, 19.84. Found: C, 67.86; H, 6.38; N, 19.68.

Mass spectrum, m/e 282; UV (95% ethanol): 233 nm .($\epsilon$23,600); 275 nm (8300), 392 nm (23,400); NMR (100 mH$_z$, DMSO-d$_6$): $\delta$ 8.61 (s, 1H, H-2), 6.36 (broad, 1H, —CH=C—CO).

EXAMPLE 2

| Tablets - Wet Granulation Formula | | |
|---|---|---|
| Ingredients | mg/tablet | mg/tablet |
| (3E)-5-(6-methylindol-3-ylmethylene-1,3-dimethyl-2-(methylimino)-4-imidazolidinone | 10 | 20 |
| Pregelatinized Starch | 10 | 15 |
| Modified Starch | 10 | 15 |
| Lactose | 166 | 244 |
| Talc | 2 | 3 |
| Magnesium Stearate | 2 | 3 |
| Total | 200 mg. | 300 mg. |

Procedure

1. Mix the (3E)-5-(6-methylindol-3-ylmethylene)-1,3-dimethyl-2-(methylimino)-4-imidazolidinone, pregelatinized starch, modified starch and lactose, mill and remix.

2. Granulate with water, dry overnight.

3. Mill the dry granulation and mix with the talc and magnesium stearate and compress.

EXAMPLE 3

| Capsules | | |
|---|---|---|
| Ingredients | mg/capsule | mg/capsule |
| (3E)-5-(6-methylindol-3-ylmethylene)-1,3-dimethyl-2-(methylimino)-4-imidazolidinone | 10 | 20 |
| Lactose | 145 | 130 |
| Cornstarch | 40 | 45 |
| Talc | 3 | 3 |
| Magnesium Stearate | 2 | 2 |
| Total | 200 mg. | 300 mg. |

Procedure

1. Mix the (3E)-5-(6-methylindol-3-ylmethylene)-1,3-dimethyl-2-(methylimino)-4-imidazolidinone, lactose and cornstarch.

2. Add the talc and magnesium stearate, mix and fill into capsule shells.

EXAMPLE 4

| Tablets - Direct Compression Formula | | |
|---|---|---|
| Ingredients | mg/tablet | mg/tablet |
| (3E)-5-(6-methylindol-3-ylmethylene)-1,3-dimethyl-2-(methylimino)-4-imidazolidinone | 10 | 20 |
| Lactose Anhydrous DTG | 156 | 219 |
| Microcrystalline cellulose | 20 | 40 |
| Modified Starch | 10 | 15 |
| Talc | 2 | 3 |
| Magnesium Stearate | 2 | 3 |
| Total | 200 mg | 300 mg. |

Procedure

1. Mix the (3E)-5-(6-methylindol-3-ylmethylene)-1,3-dimethyl-2-(methylimino)-4-imidazolidinone, lactose anhydrous DTG, microcrystalline cellulose and modified starch.

2. Add the talc and magnesium stearate and mix.

3. Compress.

I claim:

1. A compound of the formula

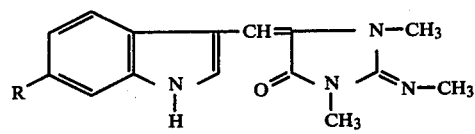

I wherein R is lower alkyl, its geometric isomers, or a pharmaceutically acceptable acid addition salt thereof.

2. A compound in accordance with claim 1, 5-(6-methylindol-3-ylmethylene)-1,3-dimethyl-2-(methylimino)-4-imidazolidinone.

3. A compound in accordance with claim 2, (3E)-5-(6-methylindol-3-ylmethylene)-1,3-dimethyl-2-(methylimino)-4-imidazolidinone.

* * * * *